(12) United States Patent
Ludwig et al.

(10) Patent No.: US 7,016,736 B2
(45) Date of Patent: Mar. 21, 2006

(54) APPARATUS FOR SUBMENTAL ELECTRICAL STIMULATION OF THE SUPRA HYOID MUSCLES OF THE FLOOR OF MOUTH

(76) Inventors: Arwed Ludwig, Kellermannstrasse 32, D-34125 Kassel (DE); Oliver-Taghi Monzavifar, Ellernstrasse 41, D-30175 Hannover (DE); Detlef Diederich, Martin-Luther-Ring 18, D-37434 Gieboldehausen (DE)

( * ) Notice: Subject to any disclaimer, the term of this patent is extended or adjusted under 35 U.S.C. 154(b) by 235 days.

(21) Appl. No.: 10/638,764

(22) Filed: Aug. 11, 2003

(65) Prior Publication Data
US 2005/0038485 A1     Feb. 17, 2005

(51) Int. Cl.
*A61N 1/18*     (2006.01)
(52) U.S. Cl. .......................................... 607/42; 607/134
(58) Field of Classification Search .................. 607/42, 607/47, 134, 46
See application file for complete search history.

(56) References Cited

U.S. PATENT DOCUMENTS

| | | | |
|---|---|---|---|
| 1,697,325 A | * | 1/1929 | Perlman ...................... 607/134 |
| 4,334,542 A | | 6/1982 | Takinishi et al. ........... 128/642 |
| 5,190,053 A | * | 3/1993 | Meer ........................... 607/134 |
| 6,212,435 B1 | * | 4/2001 | Lattner et al. .............. 607/134 |

FOREIGN PATENT DOCUMENTS

DE     297 12 412 U1     7/1997

OTHER PUBLICATIONS

Merriam-Webster Online Dictionary, (http://www.webster.com); searched: plastic.*

* cited by examiner

*Primary Examiner*—Jeffrey R. Jastrzab
*Assistant Examiner*—Alyssa M. Alter
(74) *Attorney, Agent, or Firm*—Thomas, Kayden, Horstemeyer & Risley LLP

(57) ABSTRACT

An apparatus (100) for submental electrical stimulation of supra hyoid muscles at a floor of mouth (24) includes an electrode (1) to be arranged below the tongue (22) and above a mucous membrane (30) covering the floor of mouth (24). The electrode (1) includes a form body (3) being made as one piece of plastic material. The form body (3) is designed as a negative form of the anatomic shape of the floor of mouth (24) in the region of the lower jaw arc around the frenulum of tongue (21) such that the electrode (1) may be supported in the region of the front lower jaw arc by the shape of the form body (3). The electrode (1) includes a bottom side (2) and a surface portion (4) being located at the bottom side (2). The surface portion (4) is electrically conductible. The surface portion (4) has the shape of a "U" the two free legs of which surround the frenulum of tongue (21) from two sides.

20 Claims, 4 Drawing Sheets

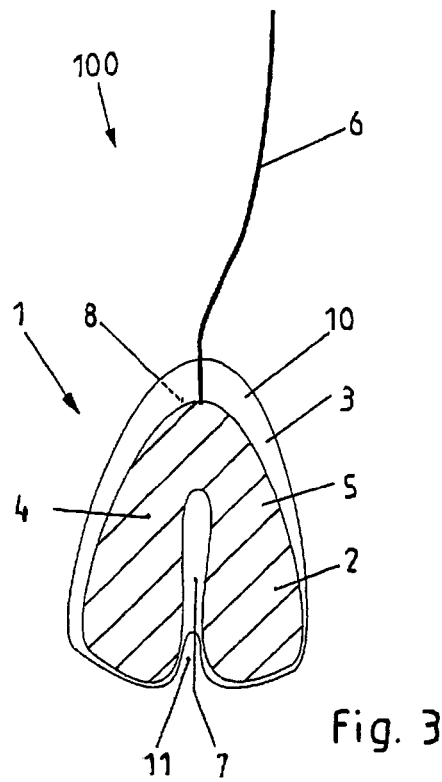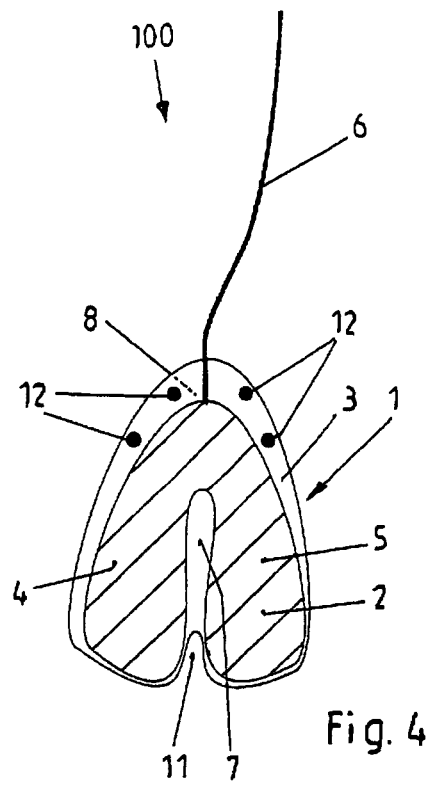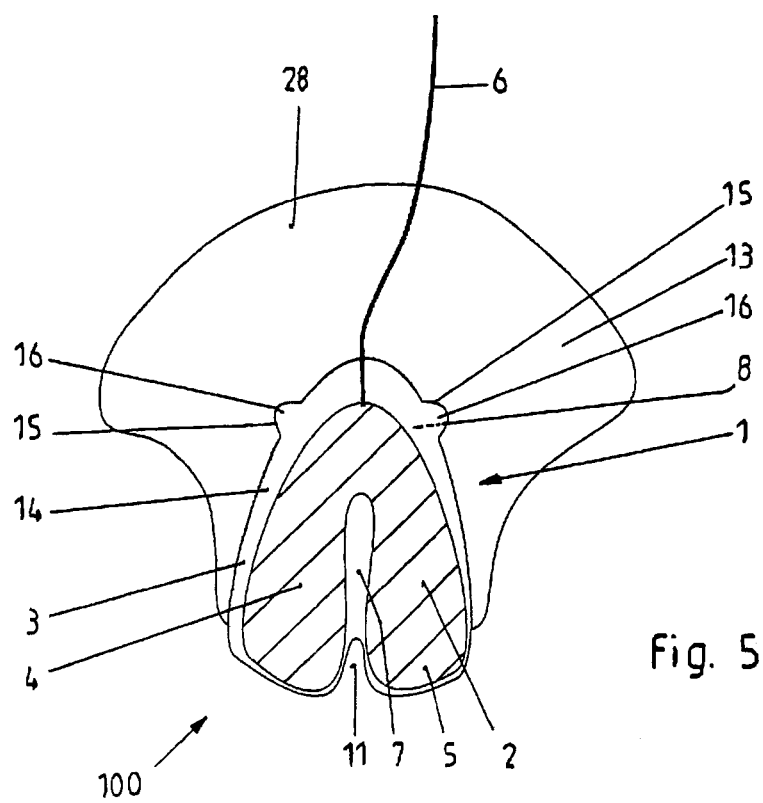

APPARATUS FOR SUBMENTAL ELECTRICAL STIMULATION OF THE SUPRA HYOID MUSCLES OF THE FLOOR OF MOUTH

FIELD OF THE INVENTION

The present invention generally relates to an apparatus for submental electrical stimulation of the supra hyoid muscles of the floor of mouth.

Such an apparatus may be used for therapy of patients suffering from the obstructive sleep apnea syndrome, meaning a breathing malfunction occurring during sleep and resulting in obstruction of the upper respiratory passages and thus snoring. During therapy, the supra hyoid muscles are strengthened by repeated electrical stimulation such that the tendency of the tongue to fall back is prevented by an increased tonus of the muscles at the floor of mouth of the patient. Such undesired falling back effects of the tongue result in obstruction of the upper respiratory passages which causes snoring. Such an apparatus may also be used to stimulate the supra hyoid muscles at the floor of mouth to pull the tongue in a forward direction during occurring obstructions.

BACKGROUND OF THE INVENTION

An apparatus for submental electrical stimulation of the supra hyoid muscles at the floor of mouth with an electrode is known from German document 297 12 412 U1. The electrode is designed to be arranged below the tongue on the mucous membrane covering the floor of mouth. The electrode at its bottom side includes an electrically conductible surface portion. The known apparatus includes a support for the electrode, the support being designed to arrange the electrode below the tongue on the mucous membrane covering the floor of mouth. The support may be designed to be supported at the set of teeth close to the floor of mouth. Preferably, it includes an individually adapted connecting plate for this purpose. Preferably, the electrode is designed as a surface electrode approximately covering the entire region of the supra hyoid muscles to be stimulated. In other words, the known electrode covers the entire inner region of the front part of the floor of mouth.

When using the known apparatus, it has been found that the surface electrode being located below the tongue only attains surface contact to the floor of mouth when there is high pressure acting upon the electrode to be presses against the soft floor of mouth. This also applies when the surface electrode is made of flexible material. In addition, when using the known apparatus, there will be undesired overstimulation of the frenulum of tongue. Consequently, carrying and using the known apparatus is not convenient to the patient. As a result, application of the known apparatus is either stopped, or it results in undesired effects without reliably achieving the desired results. These drawbacks are increased since the known apparatus is used without supervision by professional staff.

Another apparatus for submental electrical stimulation of the supra hyoid muscles at the floor of mouth with an electrode is known from U.S. Pat. No. 5,190,053. The known apparatus includes two electrodes. The two electrodes are separately connected to a common deep-drawn bar from which they extend across the floor of mouth in a fixed arrangement such that the conductible surface portions of the two electrodes contact the frenulum of tongue from both sides. The bottom sides of the electrodes are coordinated with the anatomic shape of the edge portion of the floor of mouth which they contact. In an alternative embodiment of the known apparatus, the electrodes are not coordinated with the anatomic shape. For secure contact of their electrically conductible surface portions with the floor of mouth, this alternative embodiment of the known apparatus includes spring elements engaging the common deep-drawn bar and one of the electrodes. The spring elements elastically press the electrodes towards the floor of mouth. Both alternative embodiments of the known apparatus show two substantial drawbacks. First, the electrically conductible surface portions of the electrodes are only located in the edge portions of the floor of mouth. Thus, they only extend over a comparatively small portion of the floor of mouth even in a direction parallel to the frenulum of tongue. Second, the electrodes of the known apparatus even in the embodiment including elastic support at the deep-drawn bar cannot freely yield during conventional movement of the floor of mouth caused by varying muscle tension. While the strongly limited electrically conductible surface portions result in limited effectivity of the known apparatus, support of the electrodes even in a vertical direction—meaning perpendicular to the bite plane of the lower jaw—result in substantial restriction of carrying convenience for the patient who uses the known apparatus.

SUMMARY OF THE INVENTION

The present invention relates to an apparatus for submental electrical stimulation of supra hyoid muscles at a floor of mouth. The apparatus includes an electrode being designed to be arranged below a tongue and above a mucous membrane covering the floor of mouth. The electrode includes a form body being made as one piece of plastic material. The form body is designed as a negative form of the anatomic shape of the floor of mouth in the region of the lower jaw arc around the frenulum of tongue such that the electrode may be supported in the region of the front lower jaw arc by the shape of the form body. The electrode includes a bottom side and a surface portion being located at the bottom side. The surface portion is designed to be electrically conductible. The surface portion is designed to have the approximate shape of a "U" having two free legs, the two free legs being designed to surround the frenulum of tongue from two sides. The bottom side has a shape which is coordinated with the anatomic shape of the floor of mouth. The electrode is designed to be freely movable with the tongue and the floor of mouth with respect to the lower jaw in a direction perpendicular to a bite plane.

The present invention also relates to an electrode for electrical stimulation of supra hyoid muscles at a floor of mouth. The electrode includes a body being made as one piece of plastic material. The body has a shape which is coordinated with the shape of the floor of mouth. The electrode further includes a bottom side and a surface portion being located at the bottom side. The surface portion is designed to be electrically conductible. The surface portion is designed to have the approximate shape of a "U" having two free legs, the two free legs being designed to surround the frenulum of tongue from two sides.

The novel apparatus includes an electrode to be arranged in the mouth of a patient below the tongue and above the floor of mouth. The electrode has a novel design. The electrode is coordinated and adapted to the anatomic shape of the floor of mouth by having a negative shape of the floor of mouth. In this way, there is surface contact between the electrode and the floor of mouth without undesired pressure occurring. In addition, the position of the electrode in the mouth is already stabilized due to the design of the electrode corresponding to the anatomic shape of the floor of mouth. It also may be taken into account that the electrode is pressed in a downward direction by the tongue which increases the stabilizing effect.

The electrically conductible surface portion—meaning the portion by which electrical stimulation is realized—does not cover the place where the frenulum of tongue is located. In this way, convenience of application of the novel apparatus is substantially increased for the patient. Electrical stimulation of the frenulum of tongue is prevented. Since the frenulum of tongue is not electrically stimulated, the frenulum of tongue is not tensioned, shortened or pressed against the electrode which could result in pain. Consequently, the desired arrangement of the novel apparatus in the mouth of the patient is securely maintained. Due to the fact that irritation of the frenulum of tongue by electrical stimulation is prevented to a great extent, the danger of tearing effects due to overstrain—meaning lesion—of the frenulum of tongue is eliminated. In this way, the novel apparatus guarantees painfree effective use with which the patient may stimulate the supra hyoid muscles. It has also been found that the recess of the electrode about the frenulum of tongue may be comparatively great without having drawbacks during the desired electrical stimulation of the supra hyoid muscles at the floor of mouth. In the contrary, the positive effects of the non-existing stimulation of the frenulum of tongue have the additional effect of the therapy with the novel apparatus resulting in increased success.

Preferably, the bottom side of the electrode is individually coordinated with the shape of the floor of mouth. This means that a specific electrode is manufactured for each individual patient. However, such individual manufacture is no problem since the bottom side of the electrode may be molded from a mould of the floor of mouth of the patient. Usually, an indirect mould will be used. This means that one first produces a mould of the floor of mouth of the mouth of the patient. From this first mould, one produces a model of the floor of mouth. From this model of the floor of mouth, the bottom side of the electrode is produced by molding. For example, the model of the floor of mouth is filled with artificial resin to produce the electrode. However, a deep-drawn plate may also be directly connected to the first mould to produce the electrode.

Due to the anatomic shape of the novel electrode, it is no drawback when the bottom side of the electrode and the entire electrode, respectively, are designed to be inflexible. This means that it is not necessary to design the electrode to be soft and flexible for attaining good carrying convenience of the apparatus in the mouth. In the contrary, contact of the electrically conductible surface at the floor of mouth is even improved when using a comparatively hard material for the electrode.

In an especially preferred embodiment of the novel apparatus, a layer of metal is located on the surface of the form body. The layer of metal is located in the surface portion of the electrode which is electrically conductible. For example, the metal layer may be connected to the form body by a galvanic process. For example, the plastic material of the form body may be hardened cast resin. For example, the metal layer may be a gold layer.

The electrically conductible surface portion may have the shape of a "U" to attain the desired effect of the surface portion not covering the region of the frenulum of tongue. When using such a shape, the two free legs of the "U" extend at both sides of the frenulum of tongue.

For certain applications, it may be useful to use a guiding element for the novel electrode. The guiding element is designed in a way that a relative movement of the electrode with respect to the lower jaw in a direction perpendicular to the bite plane is possible. Consequently, the guiding element does not realize a stiff guiding arrangement of the electrode with respect to the lower jaw. Thus, the exemplary embodiment of the novel apparatus including a guiding element results in improved carrying convenience without the danger of the electrode leaving its desired position between the tongue and the floor of mouth.

The novel apparatus also includes a counter electrode. The counter electrode may be supported at parts of the guiding element being fixedly connected to the lower jaw in the mouth. At its other end, the counter electrode is connected to the skin below the floor of mouth of the patient.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 3 is a top view of a third exemplary embodiment of the novel apparatus.

FIG. 4 is a top view of a fourth exemplary embodiment of the novel apparatus including supporting elements.

FIG. 5 is a top view of a fifth exemplary embodiment of the novel apparatus, the apparatus being guided with respect to the lower jaw.

DETAILED DESCRIPTION

Figure 1:
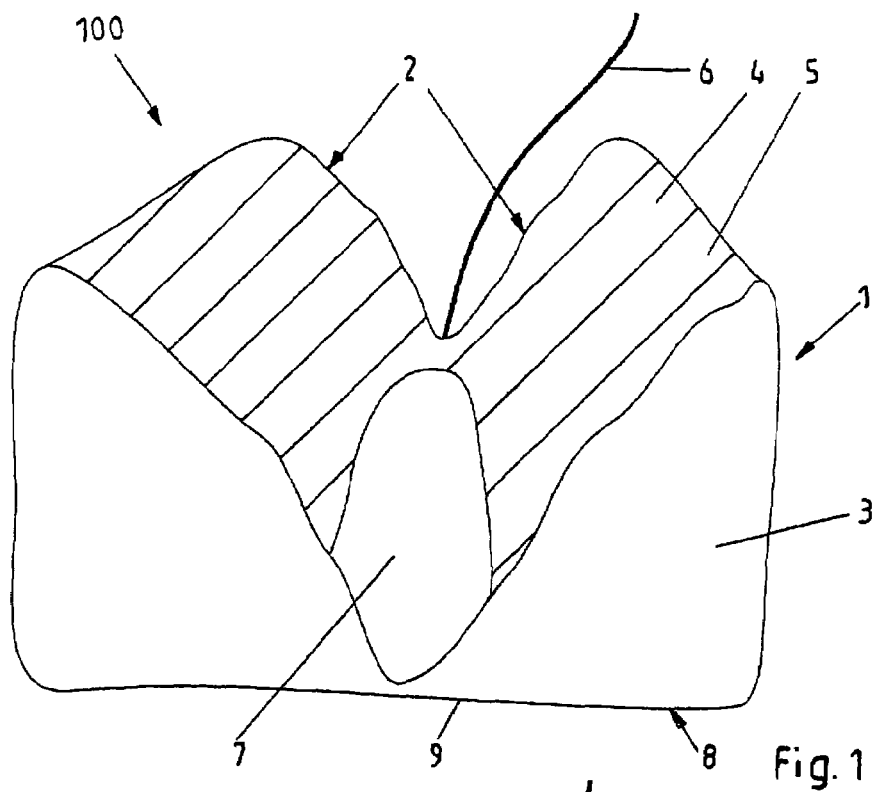
FIG. 1 is a perspective view of a first exemplary embodiment of the novel apparatus.

Referring now in greater detail to the drawings, FIG. 1 illustrates a first exemplary embodiment of the novel apparatus 100. The apparatus 100 includes an electrode 1. FIG. 1 illustrates the electrode 1 in a topside down way such that its bottom side 2 faces in an upward direction. The electrode 1 includes a form body 3 being made of plastic material. The form body 3 at the bottom side 2 includes a surface portion 4 being coated with a metal layer 5 (indicated by hatching). For example, the metal may be gold. In this way, the electrode 1 in its surface portion 4 is designed to be electrically conductible. Furthermore, the metal layer 5 is connected with a connecting line 6 to be capable of connecting the electrically conductible surface portion 4 to an electric potential. The shape of the form body 3 at the bottom side 2 corresponds to a negative form of the anatomic shape of the mouth bottom in the region of the lower jaw arc in the region of the frenulum of tongue. The surface portion 4 at the lower side 2 does not cover the region of the frenulum of tongue. At this place of the bottom side 2 of the body 3, there is a non-electrically conductible surface portion 7. The form body 3 according to FIG. 1 is designed as a more or less massive body including a plain supporting surface 9 for the tongue. The supporting surface 9 is located at the upper side 8 of the form body 3. In the illustration of FIG. 1, the upper side 8 is illustrated in the bottom portion of the drawing.

Figure 2:
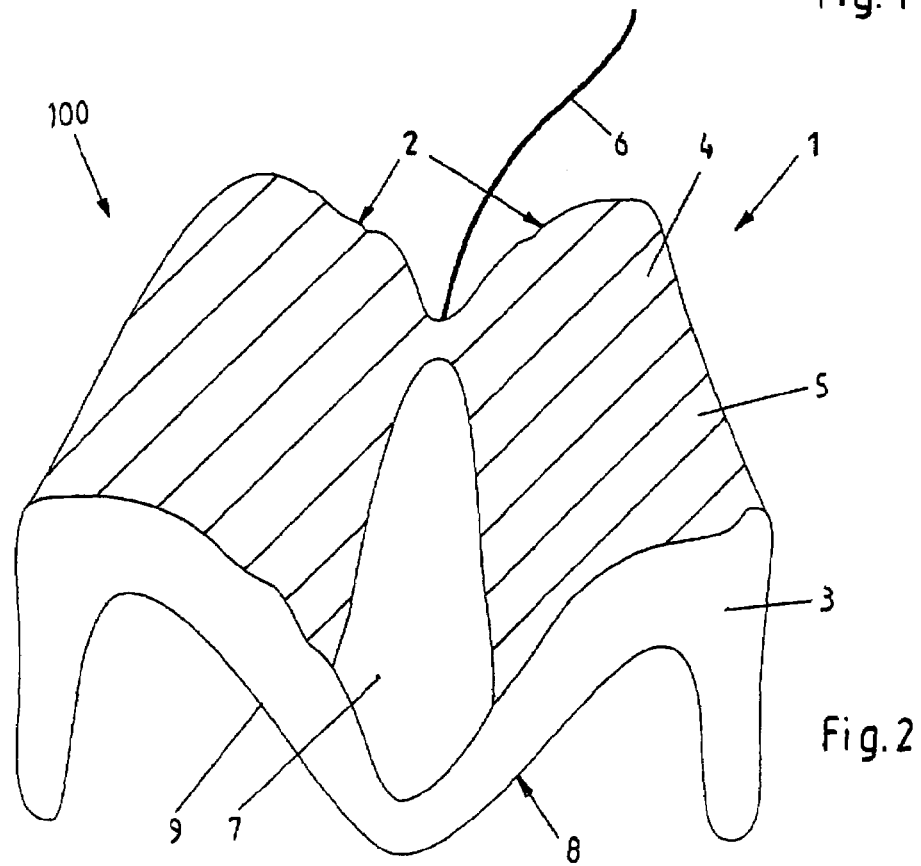
FIG. 2 is a perspective view of a second exemplary embodiment of the novel apparatus.

In the second exemplary embodiment of the novel apparatus 100 and the electrode 1 according to FIG. 2, the upper side 8 of the form body 3 is coordinated with the anatomic shape of the tongue. This means that the supporting surface 9 has a negative shape of the anatomic form of the bottom side of the tongue. In this case, the form body 3 generally has a comparatively thin wall thickness.

The exemplary embodiment of the novel apparatus 100 including the electrode 1 according to FIG. 3 is based on a form body 3 being designed as a deformed deep-drawn plate 10. Deformation of the deep-drawn plate 10 is realized in a way that its bottom side 2 attains a negative shape of the floor of mouth. The electrically conductible surface portion 4 does not extend to the edge of the form body 3, meaning it does not extend to the lower jaw at which the edge is supported. Instead, it is designed to cover the region around the frenulum of tongue in a U-shape, meaning around the surface portion 7. The form body 3 additionally includes a recess 11 serving to cooperate with the connection of the frenulum of tongue at the tongue. With this recess 11, special anatomic conditions of the respective patient can be taken into account.

The novel apparatus 100 and the electrode 1 according to FIG. 4 differ from the apparatus 100 and the electrode 1 according to FIG. 3 only with respect to the fact that it includes additional supporting elements 12. The supporting elements 12 are located in the region of the edge of the form body 3, and they serve for connection of the electrode 1 at a prosthesis. Such a design may be used when the electrode 1 is not exclusively supported by the lower jaw of a patient carrying a prosthesis, or when there is the danger of the electrode 1 colliding with the prosthesis.

The novel apparatus 100 and the electrode 1 illustrated in FIG. 5 include a guiding element 28. The guiding element 28 is designed and arranged to cooperate with the lower jaw (not illustrated). The guiding element 28 includes a connecting plate 13. The connecting plate 13 may be individually designed to correspond to the shape of the respective bottom jaw of the patient. An opening 14 is located in the connecting plate 13. The opening 14 serves for arrangement of the electrode 1. The electrode 1 is supported in a vertical direction by bars 16 engaging grooves 15. The vertical direction is to be understood as being approximately perpendicular with respect to the bite plane of the lower jaw. The other aspects of the electrode 1 illustrated in FIG. 5 correspond to the one illustrated in FIG. 3.

Figure 6:
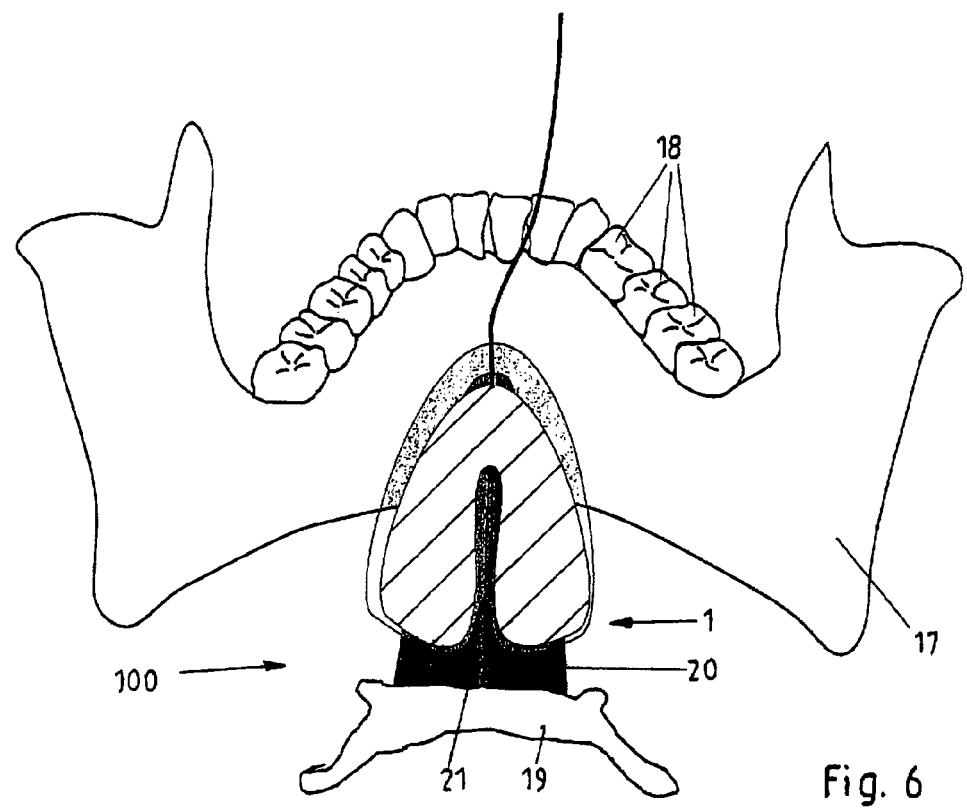
FIG. 6 is a view of the novel apparatus according to FIG. 3, the apparatus being located in the region of the lower jaw.

FIG. 6 illustrates the apparatus 100 and the electrode 1 according to FIG. 3 as being arranged in the region of a lower jaw 17 including teeth 18, a hyoid 19 and the supra hyoid muscles 20 being connected therewith. Furthermore, FIG. 6 illustrates the position of the frenulum of tongue 21 in the middle region above the supra hyoid muscles 20. The supra hyoid muscles 20 may be electrically stimulated by the electrode 1 without resulting in undesired stimulation of the frenulum of tongue 21. Due to its shape, the electrode 1 is securely located in the region of the front lower jaw arc of the mouth.

Figure 7:
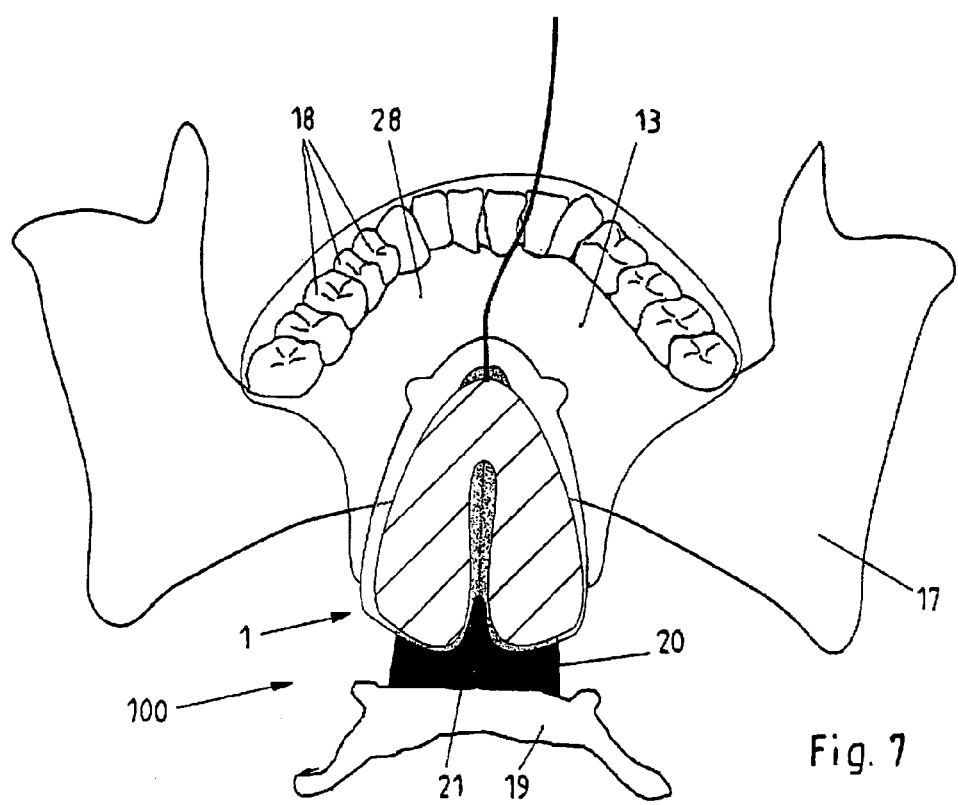
FIG. 7 is a view of the novel apparatus according to FIG. 5, the apparatus being located in the region of the lower jaw.

FIG. 7 illustrates another way of stabilizing the electrode 1. FIG. 7 also illustrates the arrangement of the electrode 1 as including the guiding element 28 according to FIG. 5. Any undesired lateral movement of the electrode 1 is prevented by the guiding element 28 including the connecting plate 13. Vertical movement of the electrode 1 is only possible in a direction perpendicular to the bite plane of the lower jaw 17. This vertical movement allows for the electrode 1 to adapt to varying tension of the floor of mouth and varying tension of the tongue being place thereon. In this way, the novel electrode 1 is much more convenient to the patient who uses the apparatus 100 including the electrode 1 compared to an inflexible arrangement of the electrode at the lower jaw as it is known in the prior art.

Figure 8:
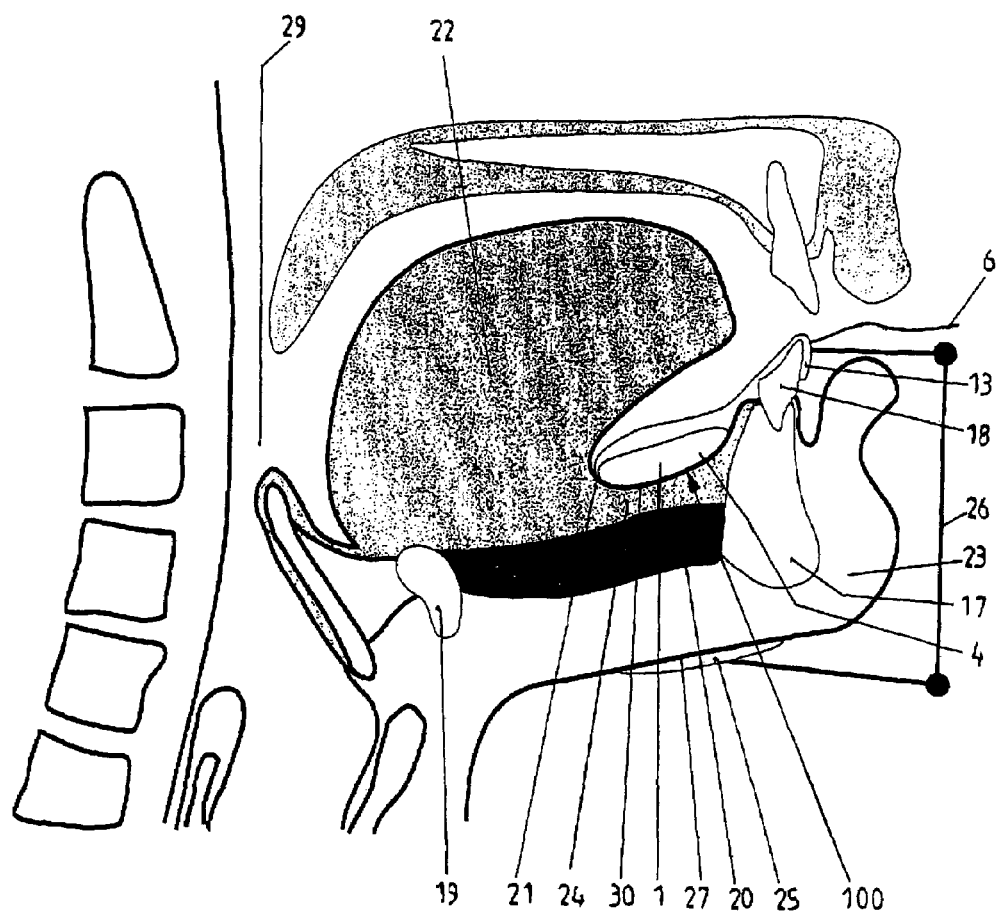
FIG. 8 is a cross-sectional view of the elements of the novel the apparatus shown in FIG. 7.

FIG. 8 generally illustrates the arrangement illustrated in FIG. 7. In addition, the mucous membrane 30 covering the floor of mouth 24 which supports the electrode 1, the tongue 22 and the soft tissue 23 surrounding the lower jaw 17 as well as the counter electrode 25 are illustrated. The counter electrode 25 is connected to the skin 27 below the floor of mouth 24 and the supra hyoid muscles 20. The counter electrode 25 is supported at the connecting plate 13 by an elastic support 26. The connecting plate 13 is designed as the guiding element 28. The counter electrode 25 is pressed against the skin 27 in an elastic way such that there is secure permanent electric contact to the skin 27. Defined voltage is fed between the electrode 1 and the counter electrode 25 for defined periods of time to attain electric stimulation of the muscles 20. In this way, the tonus of the muscles 20 may be increased over longer periods of time such that undesired backward movement of the tongue 22 during sleep is prevented. Such an undesired backward movement of the tongue 22 could lead to the respiratory passages 29 being locked.

In a preferred exemplary embodiment of the novel apparatus, the form body 3 is made of the plastic material "Pro Base Cold" of Ivoclar. This material includes approximately 97.79% PMMA and approximately 1% dibutyl phthalate. The metal layer 5 is made of galvano gold having a purity of approximately 99.97%. The material of the connecting line 6 may be chosen from different metals and metal alloys which have good conductive properties and good oxidation stability.

Many variations and modifications may be made to the preferred embodiments of the invention without departing substantially from the spirit and principles of the invention. All such modifications and variations are intended to be included herein within the scope of the present invention, as defined by the following claims.

We claim:

1. An apparatus for submental electrical stimulation of supra hyoid muscles at a floor of a mouth, comprising:
    an electrode being designed to be arranged below a tongue and above a mucous membrane covering the floor of the mouth,
        said electrode including a form body being made as one piece of plastic material,
        said form body being designed as a negative form of the anatomic shape of the floor of mouth in the region of the lower jaw are around the frenulum of the tongue such that said electrode may be supported in the region of the front lower jaw arc by the shape of said form body,
        said electrode including a bottom side and a surface portion being located at said bottom side,
        said surface portion being designed to be electrically conductible, said surface portion being designed to have the approximate shape of a "U" having two free legs, the two free legs being designed to surround the frenulum of the tongue from two sides, said bottom side having a shape which is coordinated with the anatomic shape of the floor of the mouth, said electrode being designed to be freely movable with the tongue and the floor of the mouth with respect to the lower jaw in a direction perpendicular to a bite plane.

2. The apparatus of claim 1, wherein said bottom side of said electrode has a shape which is individually coordinated with the shape of the floor of the mouth.

3. The apparatus of claim 2, wherein said bottom side of said electrode is designed as a mold which has been produced by a mold of the floor of the mouth.

4. The apparatus of claim 3, wherein said bottom side of said electrode is designed to be inflexible.

5. The apparatus of claim 2, wherein said bottom side of said electrode is designed to be inflexible.

6. The apparatus of claim 1, wherein said bottom side of said electrode is designed to be inflexible.

7. The apparatus of claim 6, wherein said surface portion of said electrode includes a metal layer.

8. The apparatus of claim 7, wherein said metal layer is designed as a galvanic layer being located on said form body.

9. The apparatus of claim 6, further comprising a guiding element being designed to be arranged to guide said electrode with respect to the lower jaw and to allow for movement of said electrode with respect to the lower jaw in a direction perpendicular with respect to the bite plane.

10. The apparatus of claim 9, further comprising a counter electrode being designed to be connected to skin below the floor of the mouth.

11. The apparatus of claim 10, wherein said counter electrode is designed to be elastically supported at parts of said guiding element to be fixed to the lower jaw arc.

12. The apparatus of claim 1, wherein said surface portion of said electrode includes a metal layer.

13. The apparatus of claim 12, wherein said metal layer is designed as a galvanic layer being located on said form body.

14. The apparatus of claim 1, further comprising a guiding element being designed to be arranged to guide said electrode with respect to the lower jaw and to allow for movement of said electrode with respect to the lower jaw in a direction perpendicular with respect to the bite plane.

15. An electrode for electrical stimulation of supra hyoid muscles at a floor of a mouth, comprising:

a body being made as one piece of plastic material, said body having a shape which is coordinated with the shape of the floor of the mouth; and a bottom side and a surface portion being located at said bottom side, said surface portion being designed to be electrically conductible, said surface portion being designed to have the approximate shape of a "U" having two free legs, the two free legs being designed to surround the frenulum of a tongue from two sides.

16. The electrode of claim 15, wherein said electrode is designed to be freely movable with the tongue and the floor of the mouth with respect to the lower jaw in a direction perpendicular to a bite plane.

17. The electrode of claim 16, wherein said bottom side of said electrode is designed to be inflexible.

18. The electrode of claim 15, wherein said bottom side of said electrode is designed to be inflexible.

19. The electrode of claim 15, wherein said surface portion of said electrode includes a metal layer.

20. The electrode of claim 19, wherein said metal layer is designed as a galvanic layer being located on said form body.

* * * * *